United States Patent

Martin et al.

[11] Patent Number: 5,181,424
[45] Date of Patent: Jan. 26, 1993

[54] TEAR-STRIP TESTING APPARATUS

[75] Inventors: James E. Martin, Mason; Richard G. Robison, Cincinnati, both of Ohio

[73] Assignee: International Paper Company, Purchase, N.Y.

[21] Appl. No.: 686,976

[22] Filed: Apr. 18, 1991

[51] Int. Cl.5 ............................................. G01N 3/08
[52] U.S. Cl. ..................................................... 73/835
[58] Field of Search .......................... 73/159, 826–831, 73/833–835

[56] References Cited

U.S. PATENT DOCUMENTS

| 521,323 | 6/1894 | Schopper . | |
|---|---|---|---|
| 1,066,447 | 7/1913 | Cleveland | 73/835 |
| 1,184,035 | 5/1916 | Scott | 73/835 |
| 1,298,138 | 3/1919 | Witham . | |
| 1,327,393 | 1/1920 | Jury | 73/833 |
| 1,423,841 | 7/1922 | Elmendorf . | |
| 1,423,842 | 7/1922 | Elmendorf . | |
| 1,447,185 | 3/1923 | Sammet . | |
| 2,473,517 | 6/1949 | Freedman | 73/827 |
| 2,674,123 | 4/1954 | Sooy . | |
| 2,983,139 | 5/1961 | Galbraith . | |
| 3,037,379 | 6/1962 | Wagner . | |
| 3,318,143 | 5/1967 | Helms . | |
| 3,580,065 | 5/1971 | Strittmater | 73/827 |
| 4,133,203 | 1/1979 | Walter . | |
| 4,596,152 | 6/1986 | Lehtikoski . | |

Primary Examiner—Robert Raevis
Attorney, Agent, or Firm—Walt Thomas Zielinski

[57] ABSTRACT

An apparatus for testing the tear strength of a tear strip in a paperboard blank. The blank is placed on and clamped to the apparatus, the latter having a force gauge mounted on it. One end of a flexible wire has a clip fastener which is attached to the end of the pull tab in the paperboard blank. The other end of the flexible wire is attached to the force gauge, the gauge measuring the amount of force required to rip the tear strip from the surrounding paperboard blank. In one embodiment of the invention, a motor is mounted on the apparatus and pulls the force gauge, the flexible wire passing around a pulley mounted on the apparatus and leading to the clip fastener. In another embodiment, the flexible wire passes over several pulleys, one of which is secured to a travelling, non-rotating nut. The nut is carried by a threaded rod rotatably journaled in the frame. A motor is coupled to the rod to rotate it, thereby pulling on the clip fastener upon movement of the nut.

4 Claims, 2 Drawing Sheets

TEAR-STRIP TESTING APPARATUS

BACKGROUND OF THE INVENTION

This invention relates to an apparatus for testing tear strips in paperboard cartons. Paperboard cartons are often provided with tear strips to facilitate carton opening for dispensing of the contents. During manufacture of the blanks for such cartons, the blanks are scored or otherwise weakened along predetermined parallel lines to form a tear strip or along lines at an angle to each other if only a limited tearing of the carton is desired.

During manufacture of blanks having tear strips, it is at times desired to check the integrity and uniformity of the scoring or weakening, so as to maintain constant depth and width of the scores or other weakening to ensure uniformity of the pull required to initiate and to sustain ripping of the tear strip away from the surrounding portion of the carton blank. During the scoring process, for example, scoring dies or other conventional scoring apparatus can become dulled, or the desired force between scoring dies and an anvil can vary, visually unnoticeable by personnel operating the scoring apparatus.

The prior art is aware of tear strip testing devices, as may be seen by reference to U.S. Pat. Nos. 2,983,139 issued to Galbraith et al., 3,037,379 issued to Wagner et al., and 3,318,143 issued to Helms.

SUMMARY OF THE INVENTION

According to the practice of this invention, an apparatus for testing tear strips includes a frame provided with one or more pulleys and a pair of clamps. The clamps are adjustably mounted on the frame for holding an edge of a sample paperboard blank which is to be tested. A clip is attached to the free end of the tear strip which is grasped by a consumer, with the clip secured to one end of a flexible cable or wire. The flexible wire passes over one or more pulleys, with the wire being pulled by a motor to initiate rupture of the tear strip along its perforations or weekened portions. A force gauge, typically mounted on the frame, is connected to the other end of the flexible wire and registers on a scale which measures the force or its analog at which the tear strip commences ripping away from the blank, and also the force required to sustain ripping.

In one embodiment of the invention, the flexible wire passes around a plurality of pulleys, with one of the pulleys secured to a travelling, non-rotating nut. The nut is threadably mounted on an elongated, threaded shaft, the latter rotated by a motor. In another embodiment of the invention, both the motor and the force gauge are mounted on the frame, with the flexible wire passing over a single pulley.

DETAILED DESCRIPTION OF THE INVENTION

Figure 1:
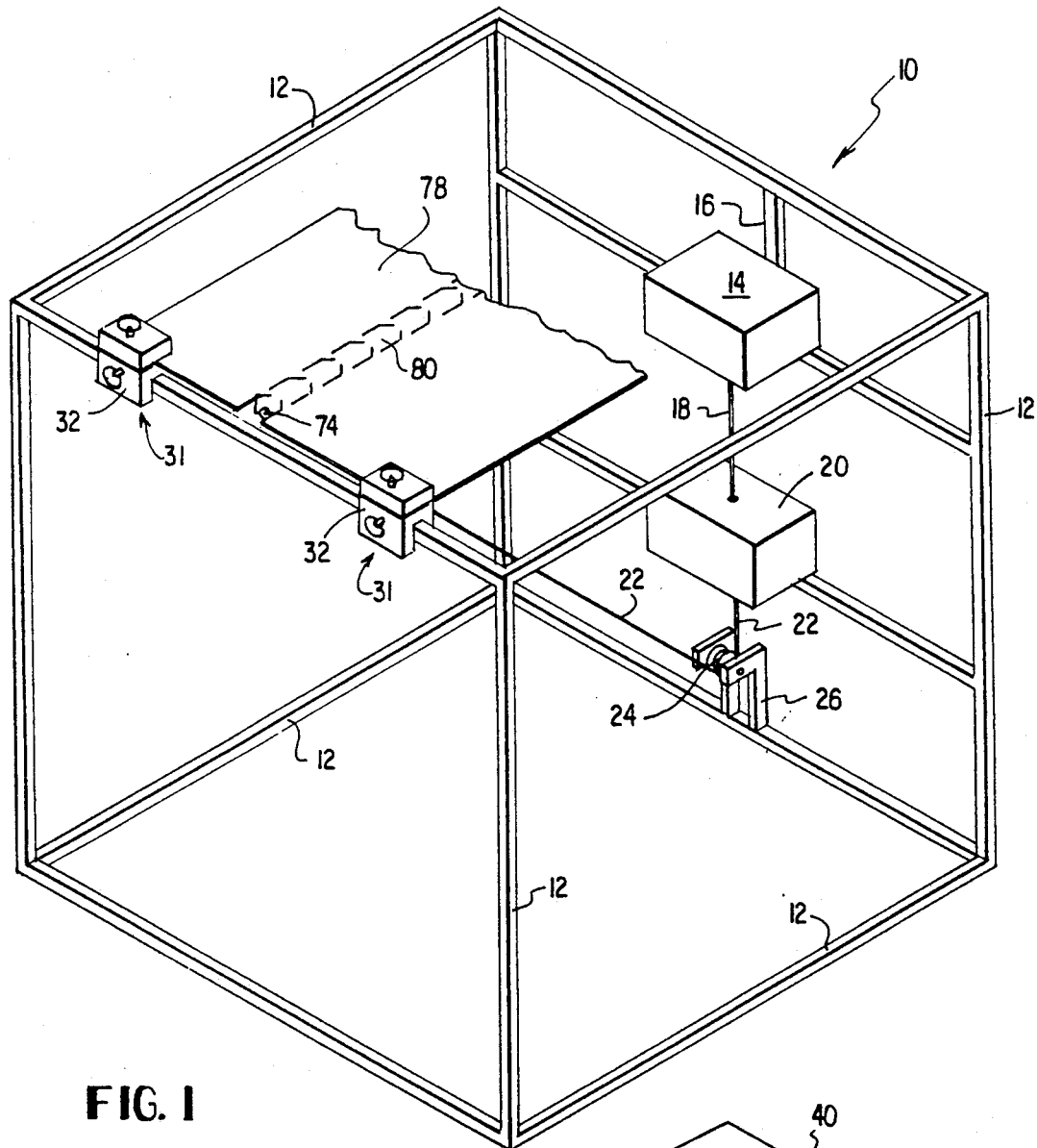
FIG. 1 is a perspective view, partially schematic, illustrating a first embodiment of the invention.
Figure 2:
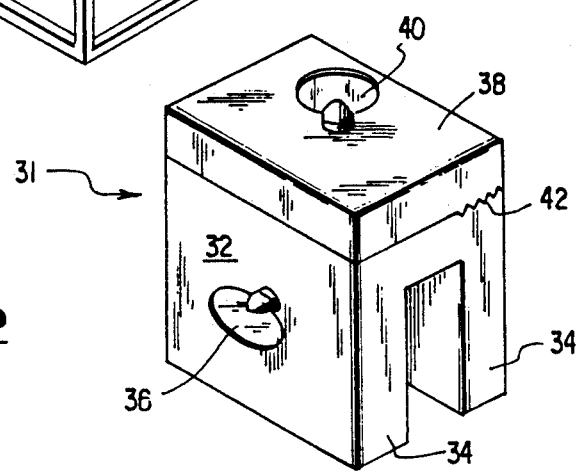
FIG. 2 is a perspective view of a clamp used in both embodiments of the invention.

Referring now to FIG. 1 of the drawings, the numeral 10 generally denotes the apparatus of this invention according to a first embodiment. A rectangular frame 12, typically fashioned from metal or other rigid bar elements, carries the various elements to be described. While illustrated as integral, frame 12 is preferably composed of a plurality of straight bars or rods joined together by angle irons, sleeve couplings, or other known rod joints. An electric motor mechanism 14 (motor and associated conventional gearing and drum) is rigidly secured and carried by frame 12, as by mounting on bracket 16 fixed to the frame. A flexible wire or other cable element 18 is secured to the motor, such that upon motor actuation wire 18 is drawn up into the motor mechanism and wound onto a drum thereon. Flexible wire 18 is connected to force gauge 20. Another flexible wire 22 is secured to the force gauge and thence passes around fixed pulley 24 mounted on the frame 12 by means of a bracket 26. The other end of wire 22 (that end not connected to the force gauge) is connected to a clip 74 (See also FIG. 3). The clip is attached to the free end of a tear strip 80 on a sample or specimen paperboard blank 78. The free end of the tear strip is that end which the user of a paperboard carton would grasp to pull. At times, as for example with rev-cut (reverse cut) tear strips, the free or pulling end of the tear strip must be displaced from the plane of a surrounding panel to permit its attachment to clip 74. Force gauge 20 is illustrated as secured to frame 12, with the operation being such that motion of wire 18 relative to the force gauge causes an actuation of the gauge with a consequent force reading corresponding to the tension in flexible cables 18 and 22. The force gauge may either be of the analog type or any other type. The force gauge may include a drum around which a single flexible wire is wound, with drum rotation being assisted by a biasing spring, as is known. In that case, the wires 18 and 22 may be the same wire.

Figure 4:
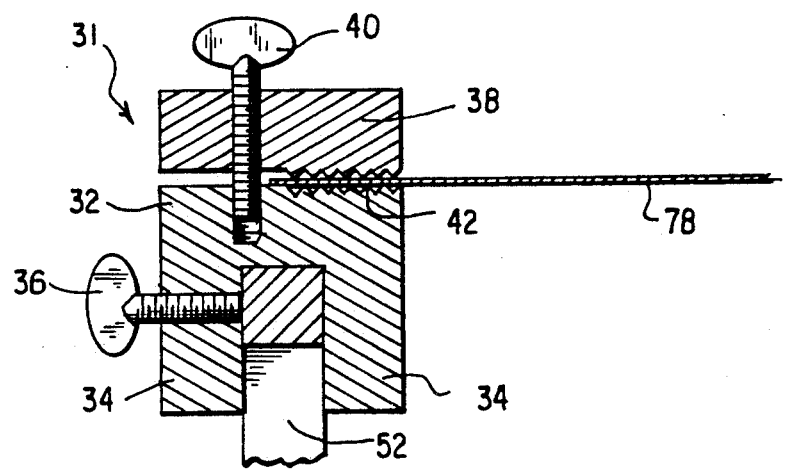
FIG. 4 is a cross-sectional view of the clamp of FIG. 2 clamping a sample paperboard blank.

Each of a pair of clamps 31 is slidably mounted along one top portion of frame 12. Each clamp 31 includes main body portion 32 having a pair of depending and spaced legs 34 which span a top elongated frame rail portion. A winged bolt 36 is threadedly mounted into one side of the clamp, with its free end abutting the frame member, as shown at FIG. 4. Thus, after positioning each of the clamps 31 along the frame member to a desired spaced-apart position, threaded bolt 36 is turned to engage the frame member and thereby fix the clamp relative to the frame. The top of each clamp 32 is provided with a generally rectangular block portion 38 which threadedly receives another wing bolt designated as 40. Corresponding edges of block 38 and clamp portion 32 are preferably knurled or roughened, as indicated by 42. Portions 42 of each clamp 31 receive an edge of a paperboard blank 78 to be tested, with manual turning of bolt 40 causing a biting action on the edge of the blank to thereby firmly secure the blank to the frame. Preferably, the frame rail portion which carries clamps 31 is marked by indicia to ensure proper relative positioning of both clamps. With the paperboard blank 78 fixed on the frame by means of clamps 31, clip 74 is manually fastened to the free end of tear strip 80 in the blank. The motor 14 is now actuated by suitable controls, not illustrated, and flexible wire 18 is caused to move into motor mechanism 14, as by winding around a drum associated therewith, to actuate the force gauge by pulling wire 18 and hence clip 74 and tear strip 80 by wire 22. This continues until the tear strip ruptures and continues to rupture from the remainder of the sample blank 78. This rupture force is registered on force gauge 20.

Figure 3:
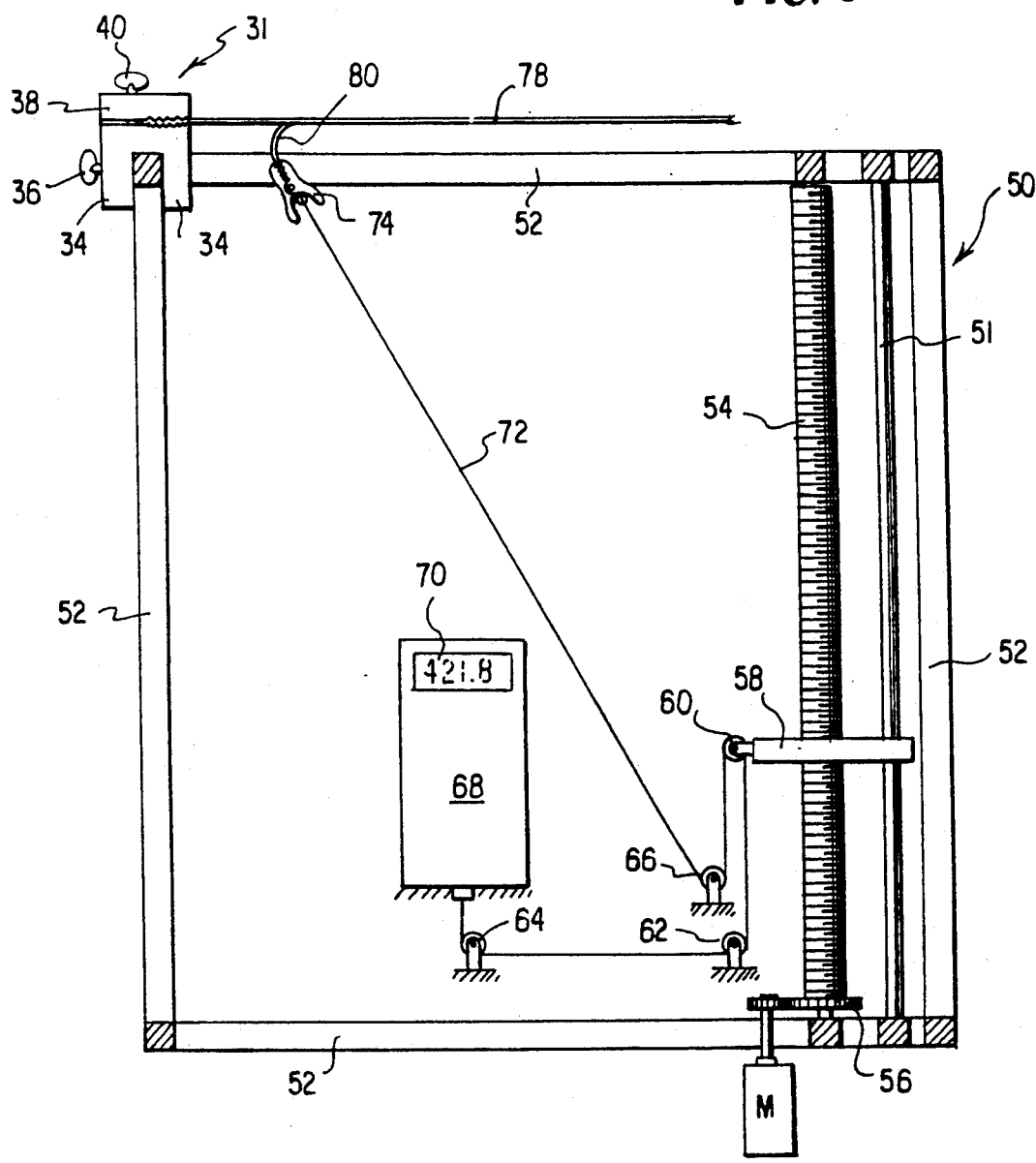
FIG. 3 is a side elevational view, partially schematic, illustrating a second embodiment of the invention.

Referring now to FIG. 3 of the drawings, another embodiment of the invention is illustrated and is denoted generally by the numeral 50. A frame 52, similar to frame 12 of the first described embodiment, carries an elongated and threaded shaft 54 journaled therein for rotation. One end of shaft 54 is provided with a gear 56 or other means for receiving rotary power from a motor M or other rotary driving mechanism. The motor M carries a gear which meshes with gear 56, or the coupling may be made by a pulley and belt connection. In this embodiment, the motor is not mounted on the frame, but may be mounted fixedly relative thereto.

A travelling nut 58 is threaded on shaft 54 for movement along the shaft, in all respects similar to element 36 of the noted Helms patent, as it nonrotatably travels parallel to the axis of threaded rotary shaft 54. Nut 58 is provided with a notch or opening for engagement with a rod 51 carried by frame 50 to prevent nut rotation upon rotation of threaded shaft 54. A pulley 60 is fixably mounted on and carried by nut 58, with other pulleys 62, 64 and 66 fixedly mounted on frame 52. As indicated, the exact location of pulleys 62, 64, 62 on frame 50 is not critical, it being only necessary that they be fixably mounted. A force gauge 68 is also mounted on the frame, the force gauge having a readout window schematically designated as 70. The readout may be of the digital or analog type. A flexible wire or cable 72 passes from force gauge 68 and passes around pulleys 64, 62, 60 and 66 as illustrated. The other end of wire 72 is connected to a clip 74, the latter manually attached to the free end of a tear strip on a paperboard blank sample to be tested. For convenience in description, the same blank-gripping clamps 31 previously described are illustrated at FIG. 3 and serve the same purpose, namely, clamping an edge of a blank sample which is to be tested. In FIG. 3, the blank is again indicated as 78 and clip 74 is illustrated as engaging the free end of tear strip 80, with the tear strip beginning to separate from the plane of the blank.

In operation, threaded shaft 54 is rotated by driving gear 56, with nut 58 moving upwardly. Initially, with nut 58 moving upwardly and clip 74 secured to the free end of a tear strip, there will be no motion of that part of wire 72 which is attached to the clip. This is because ripping of the tear strip has not yet taken place. However, upward motion of nut 58 is sensed by force gauge 68, because the lower run of wire 72 will translate, parallel to its longitudinal axis, prior to ripping. Force gauge 68 continues to register or sense the motion of nut 58, corresponding to this translation, until such time as tear strip 80 commences ripping, with clip 74 now moving towards pulley 66. Thus, prior to rupture of the tear strip, force gauge 68 is registering the tension in the lower run of cable 78. Upon rupture, commencement and thereafter registration continues until personnel conducting the test terminate it and remove the now ruptured sample blank from the apparatus in readiness for subsequent tests.

We claim:

1. An apparatus for testing tear strips in paperboard blanks, the apparatus including a rigid frame, the frame carrying a first clamp for clamping a paperboard blank having a tear strip, a force gauge carried by the frame, a flexible wire having one end attached to the force gauge and having its other end attached to a clip adapted to be attached to the free end of a tear strip on a paperboard blank, a first pulley, said first pulley fixedly attached to the frame, the flexible wire passing around the first pulley, means for exerting a pull on the flexible wire so as to move the clip in a direction generally toward the fixed pulley said force gauge fixedly attached to said frame, and wherein said means includes a threaded, rotatable rod carrying a non-rotating nut movable along the rod upon rotation of the rod, said threaded rod adapted to be rotatably coupled to a motor, the non-rotating nut carrying a second pulley, the flexible wire passing around the second pulley, whereby rotation of the threaded rod causes the second pulley to exert a pull on the flexible wire.

2. An apparatus for testing tear strips in paperboard blanks, the apparatus including a rigid frame, first and second clamps, said first and second clamps slidably mounted on the frame, said first and second clamps each including a clamping jaw to clamp a respective edge portion of a paperboard blank, said first and second clamps being movable towards and away from each other to thereby clamp spaced edge portions of an edge of a paperboard blank, a force gauge, a flexible wire having one end attached to the force gauge and having its other end attached to a clip adapted to be attached to the free end of a tear strip on a paperboard blank, means for exerting a pull on the wire.

3. The apparatus of claim 2, wherein said means includes a pulley over which said wire passes, said pulley located between the ends of said wire, said pulley being movable with respect to said frame to increase tension in said wire.

4. The apparatus of claim 2 wherein said means includes a pulley over which said wire passes, said pulley located between the ends of said wire, said pulley being fixed to said frame.

* * * * *